(12) United States Patent
John et al.

(10) Patent No.: US 11,951,251 B2
(45) Date of Patent: Apr. 9, 2024

(54) DUAL-PRESSURE RESPIRATORY ASSISTANCE DEVICE

(71) Applicants: Anna John, Portage, MI (US); Stephen John, Portage, MI (US)

(72) Inventors: Anna John, Portage, MI (US); Stephen John, Portage, MI (US)

( * ) Notice: Subject to any disclaimer, the term of this patent is extended or adjusted under 35 U.S.C. 154(b) by 857 days.

(21) Appl. No.: 17/044,715

(22) PCT Filed: Apr. 4, 2019

(86) PCT No.: PCT/IB2019/052768
§ 371 (c)(1),
(2) Date: Oct. 1, 2020

(87) PCT Pub. No.: WO2019/193535
PCT Pub. Date: Oct. 10, 2019

(65) Prior Publication Data
US 2021/0093811 A1    Apr. 1, 2021

Related U.S. Application Data

(60) Provisional application No. 62/653,512, filed on Apr. 5, 2018.

(51) Int. Cl.
*A61M 16/00* (2006.01)
*A61M 16/06* (2006.01)
(Continued)

(52) U.S. Cl.
CPC .... *A61M 16/0003* (2014.02); *A61M 16/0057* (2013.01); *A61M 16/06* (2013.01);
(Continued)

(58) Field of Classification Search
CPC .. A61M 16/00; A61M 16/0003; A61M 16/08; A61M 16/0866; A61M 16/0875;
(Continued)

(56) References Cited

U.S. PATENT DOCUMENTS 4,060,576 A * 11/1977 Grant ................. A61M 16/1095
261/153
5,943,473 A * 8/1999 Levine ................. A61M 16/167
392/401
(Continued)

FOREIGN PATENT DOCUMENTS

CN    102438571    5/2012
CN    202822380    3/2013
(Continued)

OTHER PUBLICATIONS

International Search Report of corresponding PCT Application No. PCT/IB2019/052768, dated Aug. 22, 2019.

*Primary Examiner* — Colin W Stuart
(74) *Attorney, Agent, or Firm* — Gardner, Linn, Burkhart & Ondersma LLP

(57) ABSTRACT

A respiratory system provides bi-level pressure using a dual pressure device in fluid communication with a source of breathable gas and a patient interface. The dual pressure device includes a pipe submerged in a liquid in a container, and a float disposed along the pipe. The float cyclically moves up and down the pipe between a lower position and an upper position as the floats buoyancy changes. The floats position along the pipe causes the gas pressure level to alternate between a baseline pressure level and a peak pressure level by selectively blocking and unblocking an opening in the pipe, and selectively capturing and releasing gas from the float, with the maximum gas pressure being limited by the setting on a pressure relief valve.

20 Claims, 6 Drawing Sheets

(51) Int. Cl.
*A61M 16/20* (2006.01)
*A61M 16/16* (2006.01)

(52) U.S. Cl.
CPC ... *A61M 16/202* (2014.02); *A61M 2016/0027* (2013.01); *A61M 16/16* (2013.01)

(58) Field of Classification Search
CPC .......... A61M 16/0883; A61M 16/0057; A61M 16/202; A61M 16/06; A61M 16/16; A61M 16/20; A61M 16/201; A61M 16/208; A61M 2016/0027; A61M 2205/3331
See application file for complete search history.

(56) References Cited

U.S. PATENT DOCUMENTS

| | | | |
|---|---|---|---|
| 8,720,439 B1 * | 5/2014 | Kolkowski | A61M 16/16 128/204.21 |
| 10,688,273 B2 | 6/2020 | Gustafson et al. | |
| 2004/0050386 A1 | 3/2004 | Levine | |
| 2005/0072470 A1 | 4/2005 | Jacobs et al. | |
| 2008/0149099 A1 | 6/2008 | Doyle | |
| 2011/0079222 A1 | 4/2011 | DiBlasi et al. | |
| 2012/0024286 A1 | 2/2012 | Boring | |
| 2012/0160242 A1 | 6/2012 | Gutiérrez Fonseca et al. | |
| 2012/0285454 A1 | 11/2012 | Nibu et al. | |
| 2013/0228177 A1 * | 9/2013 | Schueller | A61M 16/16 128/203.29 |
| 2013/0269693 A1 | 10/2013 | Neatrour et al. | |
| 2014/0166012 A1 | 6/2014 | Steg et al. | |
| 2014/0166013 A1 | 6/2014 | Stenzler et al. | |
| 2015/0048530 A1 * | 2/2015 | Cheung | A61M 16/024 261/135 |
| 2016/0129212 A1 | 5/2016 | Dimatteo et al. | |
| 2016/0310689 A1 | 10/2016 | Osborne et al. | |
| 2017/0281051 A1 | 10/2017 | Evans et al. | |

FOREIGN PATENT DOCUMENTS

| | | | |
|---|---|---|---|
| WO | 2006004439 | 1/2006 | |
| WO | 2012020387 | 2/2012 | |
| WO | 2014026227 | 2/2014 | |
| WO | WO-2016115465 A1 * | 7/2016 | .......... A61M 16/201 |

* cited by examiner

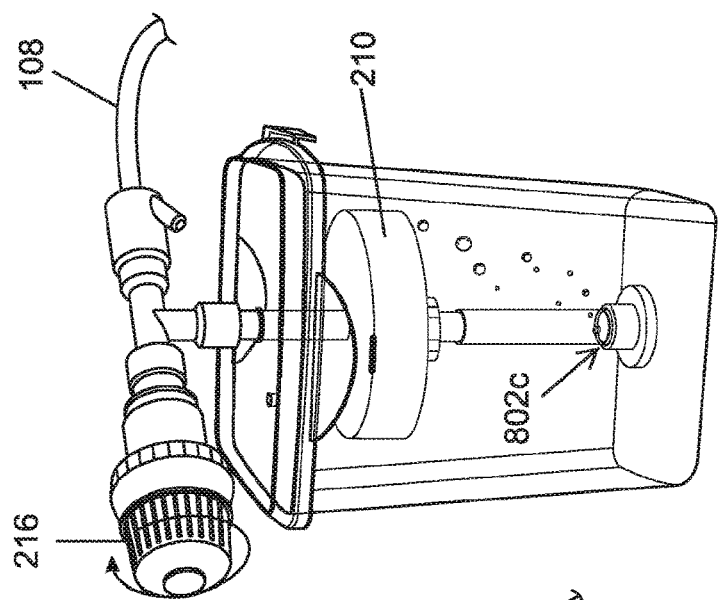
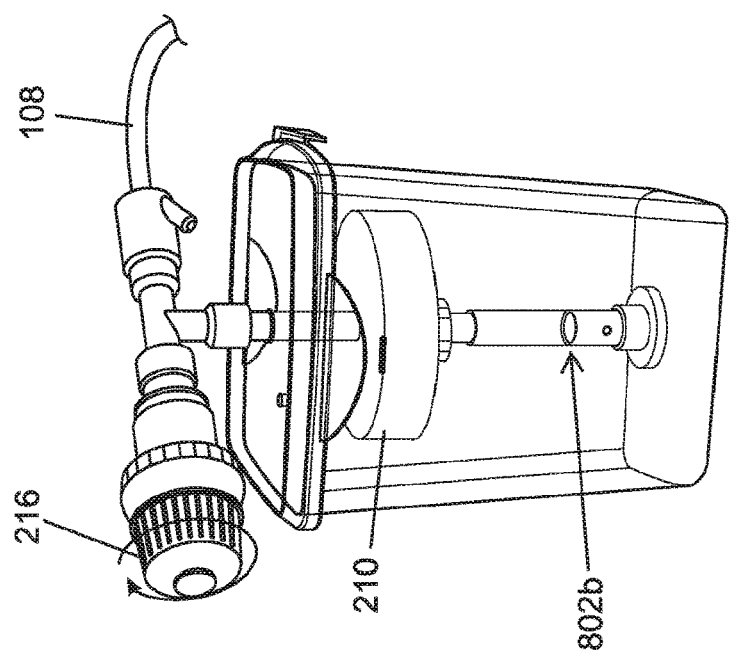
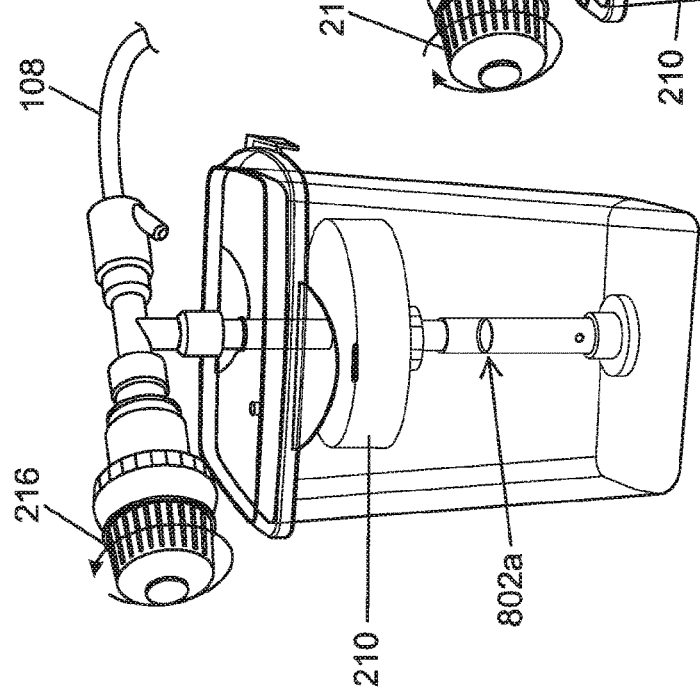

DUAL-PRESSURE RESPIRATORY ASSISTANCE DEVICE

CROSS REFERENCE TO RELATED APPLICATIONS

The present application is a § 371 national stage of International Application PCT/IB2019/052768, filed Apr. 4, 2019, which claims the benefit of U.S. provisional Pat. Application Ser. No. 62/653,512, filed Apr. 5, 2018, both of which are hereby incorporated herein by reference in their entireties.

FIELD OF THE INVENTION

The present invention is directed to respiratory assistance devices, and in particular, to bubble respiratory assistance devices.

BACKGROUND OF THE INVENTION

Infant respiratory distress is a significant problem worldwide. Such respiratory illnesses are a leading cause of death for children under 5 years of age. Continuous Positive Airway Pressure (CPAP) is a widely used treatment for infant respiratory distress. The constant pressure recruits (opens collapsed portions of) and stabilizes (keeps open those previously collapsed portions of) the functional units of the lung, the alveoli. One low cost, low tech mechanism of delivering this treatment, bubble CPAP, utilizes an air tube submerged in a column of a fluid such as water (such as in a suitable container filled with water), where the submerged depth of the bubbling air-water interface sets and indicates the backpressure delivered by the device. With the air tube submerged in the water column, air bubbles escape out of the bottom of the air tube. Thus, within the air tube and associated patient respiratory tubing, the resulting backpressure is directly proportional to the submerged depth of the tube.

Bubble continuous positive airway pressure (bubble-CPAP) devices are a safe and effective solution for treating infants in respiratory distress worldwide. An end portion of the bubble CPAP respiratory tubing of (the expiratory limb) is submerged in a column of water (that is, the end portion of the respiratory tubing is inserted into a container filled with water to a prescribed depth) to set and indicate the pressure of air provided to the patient interface of the bubble CPAP. The patient interface may include a mask or occlusive prongs.

Sicker infants often require additional treatments, such as bi-level positive airway pressure or Nasal Intermittent Positive Pressure Ventilation (NIPPV) or Non-Invasive Positive Pressure Ventilation (NIPPV) to decrease their work of breathing. With NIPPV, clinicians can independently set an upper pressure level (i.e., a high pressure level), a lower pressure level (i.e., a low pressure level), and a cycling rate between the two pressure levels. Such bi-level positive airway pressure may also be used for patients with congestive heart failure, asthma chronic obstructive pulmonary disease, and sleep apnea, among other conditions.

However, NIPPV is traditionally delivered with conventional ventilators which can be very expensive, are difficult to use, and require continuous electricity to operate. Such requirements often leave much of the world without access to this treatment.

SUMMARY OF THE INVENTION

Embodiments of the present invention provide a dual-pressure positive airway system and methods. The system is relatively simple and inexpensive, and can be assembled, operated, disassembled, and cleaned with basic instruction and materials more easily than traditional NIPPV device, particularly in resource limited setting lacking staff with extensive discipline-specific training. The system can be operated without electricity provided that a source of pressurized breathing gas, such as medical air and oxygen, is available. Alternatively, the system can be operated with the benefit of an electric pump that supplies pressurized breathing gas. A small amount of water or other suitable liquid is also used to operate the system. Thus, the system can be operated to aid breathing, particularly of infants, in environments with little or no electrical power or other resources available, by persons without advanced discipline-specific training. The system may also be scaled as necessary to supply breathing gases to larger persons.

In one form of the present invention, a dual-pressure positive airway pressure system includes an air supply suitable for respiratory assistance that is coupled to a first end of a respiratory conduit with a patient interface for delivering air or other breathing gas. A second end of the respiratory conduit, opposite the first end, is coupled to a bubbler device. A pressure regulator is also coupled to the bubbler device. The bubbler device features a container for receiving a volume of water to form a hydrostatic water column, and a central pipe at least partially submerged in the column of water. An oscillatory relief mechanism is disposed along the central pipe and includes a float which captures gas bubbles released through a vent hole in the central pipe when the float is in a lower first position. The collection of gas in the float increases the buoyancy of the float. The increased buoyancy causes the float to rise through the column of water to an elevated second position, covering the vent hole in the central pipe and forcing the pressure in the respiratory conduit to increase to a higher pressure level proportional to the level or setting of the pressure regulator. When air bubbles are escaping from the vent hole, the pressure level in the respiratory conduit is at a lower pressure level proportional to the submerged depth of the escaping bubbles (pressure=density of fluid*acceleration due to gravity*height of fluid column). When the vent hole is occluded, the air instead vents from the pressure regulator, so that the pressure level in the respiratory conduit is at the level set by the pressure regulator. The air-water meniscus travels down the central pipe to a level proportional to this pressure as an indicator of pressure (pressure/density of fluid*acceleration due to gravity)=depth of air-water meniscus). Note that this air-water interface indicates but does not set the pressure: the pressure regulator sets the pressure.

A respiratory system with a bi-level pressure capability of the present invention includes an air source, a respiratory circuit (optionally with an in-line system for heating and humidification), a patient interface (such as nasal prongs or a mask), and a dual pressure device. The air source provides a flow of gas into the respiratory system. This will typically consist of a blended mixture of compressed medical air and oxygen. The dual pressure device is typically operated with water and includes a pipe submerged in the water, with a float disposed along the pipe. The float cyclically slides up and down the pipe between a lower first position and a higher second position. The float cyclically shifts the pressure level of the respiratory system between a baseline pressure level and a peak pressure level. The pressure level drops to the baseline pressure level when the float, resting in the lower first position, allows gas bubbles to escape from at least one vent hole in the pipe. The pressure level rises to the peak pressure level when the float, sliding to the higher second position, occludes the vent hole(s) in the pipe, forcing air to instead vent at the pressure regulator.

For example, for infants or young children the high or peak pressure level may be a prescribed high pressure level of about 8-25 cm $H_2O$, and the low or baseline pressure level may be a prescribed low pressure level of about 5-8 cm $H_2O$. The high and low levels may be visually measured if a manometer is connected to the respiratory conduit. The depth of the air-water meniscus in the central pipe functions as a built-in pressure manometer for the high level of pressure. The high pressure level is defined by a selected pressure level at the pressure regulator, while the low pressure level is defined by a depth of vent holes in the central tube with respect to a height of the water column.

In another aspect of the present invention, the variable cycling rate is 20-40 cycles per minutes. The variable cycling rate is defined by a selected flow rate of the air supply.

In a further aspect of the present invention, the respiratory conduit is also coupled to at least one of a humidification system and heating system that provides for a selected humidity level and/or a selected temperature level of the delivered air.

Embodiments of the present invention provide a desirable low cost and low tech solution for providing bi-level positive airway pressure to a patient through an exemplary dual-pressure respiratory assistance device.

These and other objects, advantages, purposes and features of the present invention will become apparent upon review of the following specification in conjunction with the drawings.

BRIEF DESCRIPTION OF THE DRAWINGS

FIGS. 8A, 8B, and 8C are side perspective views of the dual-pressure respiratory assistance device of FIG. 2, illustrating an adjustment of a pressure regulator of the dual-pressure respiratory assistance device to adjust a level of the high, peak pressure level, which corresponds to the varying depth of an air-water meniscus level in the central pipe.

DESCRIPTION OF THE PREFERRED EMBODIMENTS

Methods and systems of the present invention provide for a dual-pressure respiratory assistance device that utilizes a float for cycling between a low, baseline pressure level and a high, peak pressure level. The cycling between the baseline pressure level and the peak pressure level is accomplished with a single power source, e.g., an air supply. For example, the bi-level pressure level may cycle between a low, baseline pressure level, such as a prescribed pressure level during patient exhalation, and a high, peak pressure level, such as a prescribed high pressure level to assist patient inhalation. Alternatively, the cycling between a high pressure and low pressure may not directly correspond with patient respiratory efforts. The respiratory assistance device includes a pressure regulator for adjusting the high, peak pressure level. The respiratory assistance device also includes a central pipe (around which the float rises and falls) with a first set of "proximal" vent holes. The depth of these proximal vent holes (and thus the depth of the air-water interface), with respect to a depth of a column of water into which the central pipe is submerged, defines the low pressure level.

Figure 1:
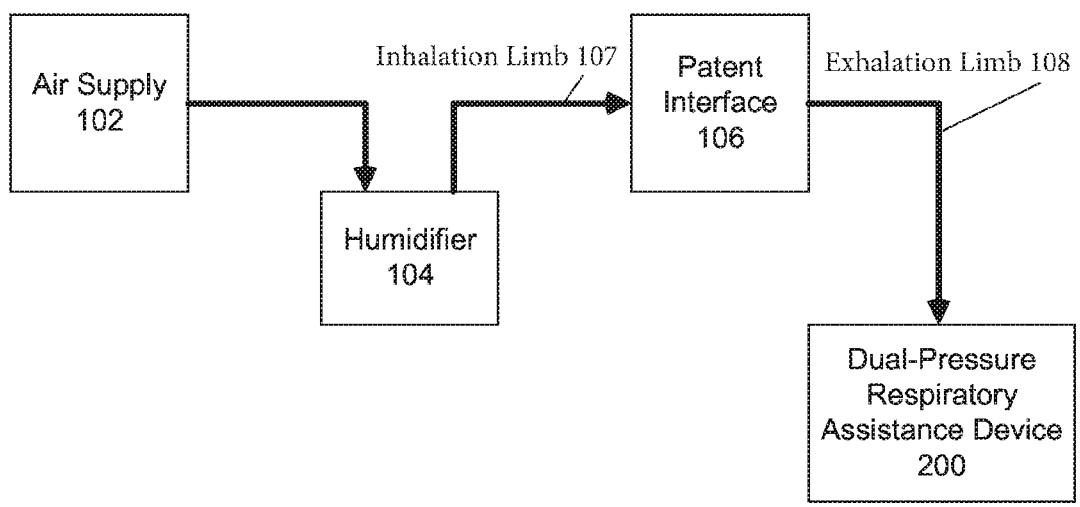
FIG. 1 is a block diagram of an exemplary respiratory delivery system that incorporates a dual-pressure respiratory assistance device in accordance with the present invention.

Referring now to FIG. 1, an exemplary dual-pressure respiratory assistance device 200 is incorporated into a respiratory delivery system 100. The air supply 102 provides breathable gas suitable for respiratory assistance (e.g., medical grade compressed air). The air supply 102 may incorporate an exemplary air/oxygen blender for blending in a desired quantity of compressed oxygen into a supply of medical grade air. The air supply 102 may also include a valve and flowmeter for controlling and measuring the flow of air or blended air/oxygen. The flowmeter provides a measurement of a quantity of air, oxygen, or blended air, such as a measurement of liters of gas per minute (L/min). The air or air/oxygen mixture is optionally passed through an inline humidifier 104 which is configured to humidify the supplied air to a desired humidification level. Optionally, the humidifier 104 is further configured to heat the supplied air to a desired temperature level. Alternatively, an additional inline device may be used to heat the supplied air. The air or air/oxygen mixture, whether or not humidified and/or heated, is then passed through a patient interface 106, which may include a mask or occlusive prongs. The air provided to the patient interface 106 may be considered to be part of an inhalation limb 107 of the respiratory delivery system 100, with the air exiting the patient interface 106 considered to be an exhalation limb 108 of the respiratory delivery system 100. It is this output of the patient interface 106 (the exhalation limb 108) that is coupled to the dual-pressure respiratory assistance device 200. The components of the respiratory delivery system 100 are interconnected via suitable conduits, such as plastic respiratory tubing sections. Such tubing sections may be formed with flexible or rigid sections.

As discussed herein, in conventional bubble CPAP devices, a similar system may be used, except that instead of the exhalation limb connecting to the dual pressure respiratory assistance device, the exhalation limb is now connected to a portion of tubing that is at least partially submerged into a column of water, where the depth of the tube submerged into the column of water sets and indicates the CPAP pressure. That is, air pressure forces an air-water meniscus layer all the way to the bottom of the submerged tube, allowing gas bubbles to escape from the bottom of the submerged tube.

Figure 2:
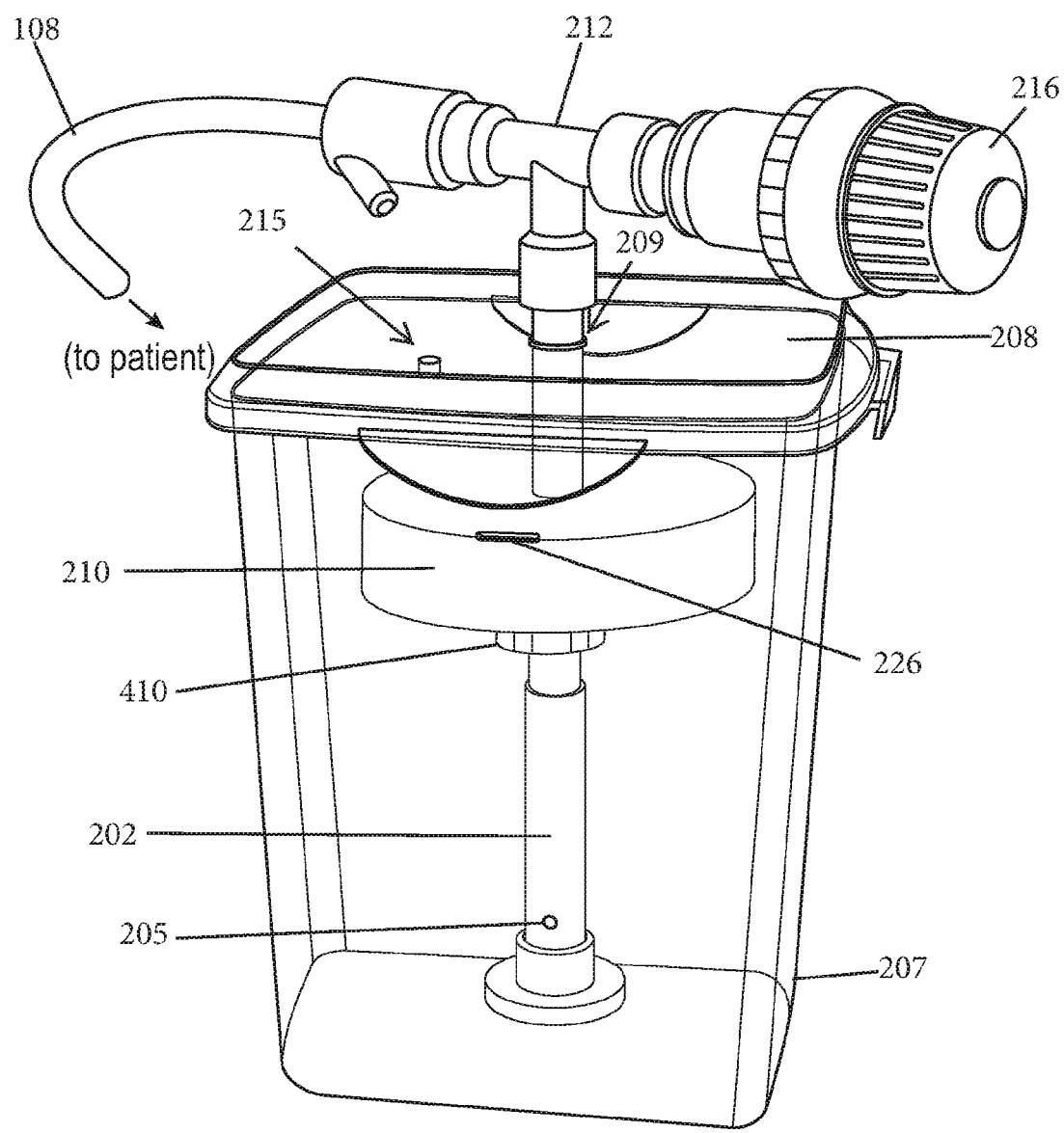
FIG. 2 is a side perspective elevation view of a dual-pressure respiratory assistance device in accordance with the present invention.

In embodiments of the present invention, such as illustrated in FIGS. 1 and 2, the exhalation limb 108 exiting from the patient interface 106 is coupled to an exemplary dual-pressure respiratory assistance device ("respiratory device") 200. As illustrated in FIG. 2, the respiratory device 200 includes a central pipe 202 that is submerged into a column of water. Suitable sources may be used, e.g., distilled water. An exemplary oscillatory or cyclical mechanism of the respiratory devices 200 comprises a variably buoyant float ("float") 210, a set of proximal vent holes 203 in the central pipe 202 that selectively release gas bubbles from the central pipe 202 (which are temporarily captured or entrapped by the float 210), and an adjustable pressure regulator or pop-off valve 216 that controls the set point for a high, peak pressure level provided to the patient interface 106.

Such dual-pressure respiratory treatment devices are also described in U.S. patent application Ser. No. 15/650,443 ("the '443 patent application"), the disclosure of which is hereby incorporated herein by reference. Exemplary embodiments of the present invention are improvements over the dual-pressure respiratory treatment devices described in the '443 patent application. For example, exemplary embodiments of the present invention utilize a single pressure regulator 216 (which can be external to the water) to continuously adjust the high, peak pressure level in less than a second, without interrupting delivery of dual pressure respiratory assistance to the patient, and without increasing the risks of adverse events such as water spillage or patient infection.

In contrast in the '443 patent publication, the peak pressure level is adjusted through the selection and exchange of high pressure pipes (bottom portion of the central pipe) with different depths for a distal vent hole, with the peak pressure level set by the depth of the distal vent holes of the high pressure pipes. While the clinician is disconnecting one high pressure pipe and replacing it with another high pressure pipe, a process which can take several seconds to a minute, treatment is interrupted; the patient is not receiving dual pressure respiratory assistance. This process necessitates reaching into the water to exchange pipes, increasing risk of infection and water spillage. Because the '443 patent application requires several different high pressure pipes, complexity is also increased (for example, high pressure pipes not in use could be lost). Furthermore, unlike embodiments described herein, the peak pressure level of the '443 patent application cannot be continuously varied. Instead, the peak pressure of the '443 patent application is only set to values for which high pressure pipes are available (e.g., 12 or 14 cm $H_2O$, but not 13 cm $H_2O$). Additionally, the '443 patent application discloses the dual pressure device coupled to the patient interface via a "patient branch," while as illustrated in FIG. 1, exemplary embodiments of the present invention utilize a inspiratory circuit that connects the dual-pressure respiratory device 200 to the expiratory limb, after (downstream of) the patient interface 106. This "patient branch" is dead-space which can lead to increased rebreathing of exhaled carbon dioxide. Embodiments of the present invention further utilize an improved central pipe 202, which eliminates several components as compared to the central pipe of the '443 patent application, for improved ease of use. Embodiments of the present invention also feature a lidded container to reduce water losses through spilling and evaporation; at least one hole in this lid may be provided to prevent the buildup of pressure in the container and also permits the addition or removal of water without opening the lid. Embodiments of the present invention are also described in U.S. provisional application, Ser. No. 62/653,512, filed Apr. 5, 2018, which is hereby incorporated herein by reference in its entirety.

The cyclical mechanism of the exemplary respiratory device 200 alternates the air pressure provided to the patient interface 106 between a low, baseline pressure level, and a high, peak pressure level. As discussed hereinabove, the baseline pressure level may be a prescribed low pressure level, and the peak pressure level may be a prescribed high pressure level. The respiratory device 200 therefore provides for a bi-phasic pressure waveform where a lower, baseline pressure level is alternatively maintained during a first duration, and a peak pressure level is maintained during a second duration. By adjusting the air flow rate at the air supply 102, the cyclic rate between the baseline and the peak pressure levels may be adjusted (e.g., between 20-40 cycles per minute). Note that, in a present embodiment, the respiratory delivery system transitions from the baseline pressure level to the peak pressure level in a period of time that is significantly less than each of the first and second periods of time. In other words, the transition times between pressure levels are not significant as compared to the periods of time the respiratory delivery system is at the baseline pressure level or the peak pressure level.

Figure 3:
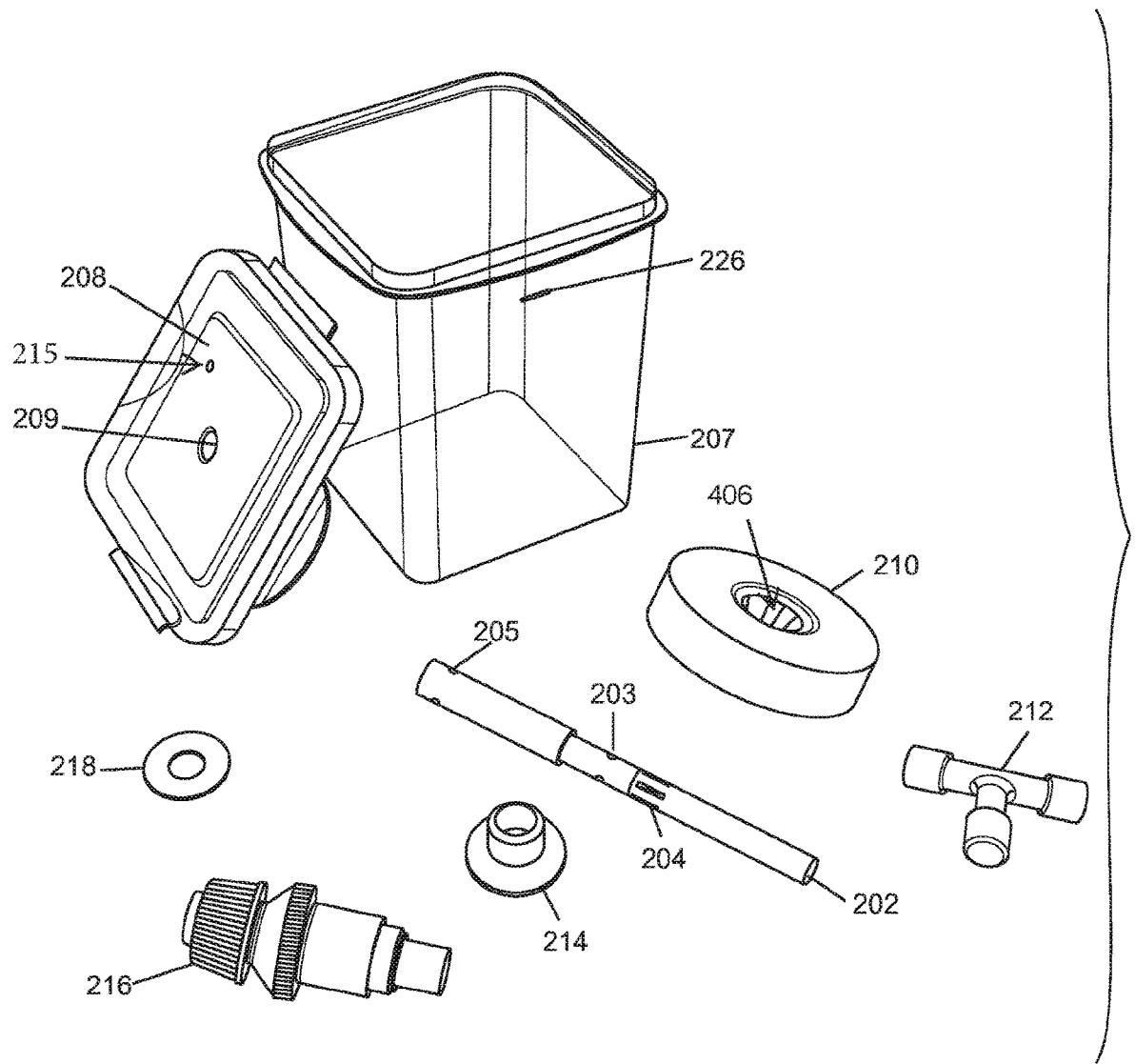
FIG. 3 is a side perspective view illustrating disassembled components of the dual-pressure respiratory assistance device of FIG. 2.

As illustrated in FIGS. 2 and 3, the column of water is enclosed within a container 207 having lid 208 to reduce water loss due to evaporation or sloshing. The container 207 may be manufactured of a variety of suitable materials, such as injection molded plastic, glass, metal, or combinations thereof, and is preferably made of a transparent material to facilitate viewing of the gas bubbles, water levels, and float operation. As illustrated in FIG. 2, the container 207 may comprise a rectangular shape or a cylindrical shape. The lid 208 may be fitted with clasps, threads, gaskets or other means for securing the lid 208 to the container 207, thus preventing loss of water. As illustrated in FIG. 2, the lid 208 is dimensionally configured to fit to the container 207. The lid 208 may also include an air vent 215. The container 207 is filled with water to form the desired column of water. A height of the column of water in the container 207 helps to define the low, baseline pressure level. One or more markings 226 may be scribed upon the container 207 for aiding in achieving a desired height of the column of water. For example, an exemplary marking 226 may be used to indicate that a water line at the marking 226 realizes a low, baseline pressure level of 5 cm $H_2O$ (that is, an air-water meniscus layer and bubbling from vent holes 203 on the central pipe 202 occurs five (5) centimeters beneath the top of the column of water). The low, baseline pressure level may be adjusted (e.g., from 5 to 8 cm $H_2O$) by varying the height of the column of water in the container 207.

As also illustrated in FIGS. 2 and 3, the respiratory device 200 may be formed of individual parts that are readily disassembled for cleaning, disinfection, sterilization, and/or storage. For example, the exhalation limb 108 of the respiratory delivery system 100 couples to the respiratory device 200 via a T-joint 212 of the respiratory device 200. As illustrated in FIG. 3, the T-joint 212 is a T-shaped plastic conduit or pipe with a pair of opposite openings and a single lower opening below the pair of openings. As illustrated in FIG. 2, the exhalation limb 108 is coupled to one side of the T-joint 212, while a pressure regulator or pop-off valve 216 of the respiratory device 200 is coupled to the opposite side of the T-joint 212. A bottom of the T-joint 212 is also coupled to an upper end of a central pipe 202 of the respiratory device 200. Connectors with varying geometry could be similarly used to couple the pressure regulator 216, exhalation limb 108, and the respiratory device 200. An exemplary central pipe 202 is an extruded plastic hollow cylinder with machined sidewall recesses such as grooves 204 formed or established on one end, a set of proximal vent holes 203 below the grooves 204, and optionally a set of distal vent holes 205 on an opposite, bottom end of the central pipe 202.

A step change in pipe diameter (larger diameter on the bottom) provides a shoulder for the float 210 to rest in the lower position. Optionally, the central pipe 202 may be made by combining two separate pipes. The bottom end of the central pipe 202 is coupled to an anchor 214 of the respiratory device 200. The anchor 214 may aid in holding the central pipe 202 to the bottom of the container 207 through its weight. A base of the anchor 214 may also be configured to aid in stabilizing the central pipe 202 when placed onto the bottom of the container 207, through friction and/or possible bonding with an adhesive agent.

Referring to FIGS. 2 and 3, and as discussed in detail below, an exemplary variable buoyancy float 210 is configured for insertion over the central pipe 202. An exemplary float 210 is of injection-molded plastic construction, with an inner sleeve and a portion for retaining escaping gas bubbles at its upper end, lower openings in the inner sleeve for controlling the escape of gas bubbles from the at least one proximal vent hole 203, and upper openings in the inner sleeve for controlling the release of gas bubbles retained by the float 210 when the float is elevated. Optionally, the lower and upper openings may be combined into a single larger opening, as in a vertically oriented slot, that both admits gas from the vent hole 203 at its lower end, and vents the gas through the grooves 204 at its upper end.

The variable buoyancy float 210 is fitted with a weighted washer 218 to provide a negative buoyancy for the float 210, although it is envisioned that the float itself may be made from denser-than-water material, such as polymeric resin, which may obviate the need for a separate weight. The float's negative buoyancy is overcome when the float 210 retains a sufficient collective volume of the escaping gas bubbles and takes on a positive buoyancy. It is envisioned that additional or different weights may be selected to adjust the overall weight of the float and, thus, the volume of gas that must be collected by the float before it will become buoyant.

The float 210, fitted with the weighted washer 218 (to provide a negative buoyancy that is offset when air bubbles are retained within the float 210), is inserted over the central pipe 202. As illustrated in FIG. 2, the central pipe 202, float 210, and weighted washer 218, are inserted into the container 207. Once the lid 208 has been fastened on, the upper end of the central pipe 202 will extend from out of the container 207, via a hole 209 positioned in the center of the lid 208. Before the lid 208 is secured, the container 207 will be filled with water to create a column of water to the scribed mark 226 Note that the level of water can be adjusted (after securing the lid 208) through the air vent 215. The T-joint 212 is coupled to the upper end of the central pipe 202. The exhalation limb 108 of the respiratory delivery system 100 couples to one side of the T-joint 212, while the pressure regulator 216 couples to the opposite side of the T-joint 212.

Figure 4:
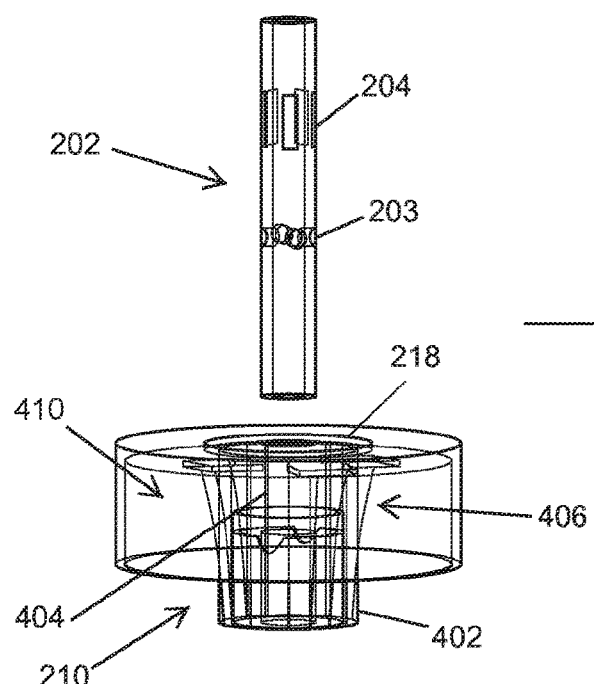
FIGS. 4 and 5 illustrate a central pipe inserting into and interacting with a float of a dual-pressure respiratory assistance device.
Figure 5:
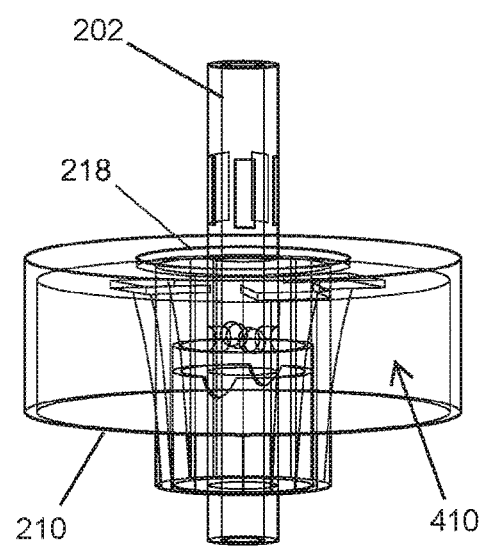

FIGS. 4 and 5 further illustrate the float 210 and corresponding central pipe 202 of the respiratory device 200 of FIGS. 2 and 3 It should be understood that in FIGS. 4 and 5, only an upper portion of the central pipe 202 is illustrated. That is, the bottom or lower portion of the central pipe 202 (see FIG. 3) is the same, and are therefore is omitted for the sake of clarity.

As illustrated in FIG. 4, the upper portion of the central pipe 202 has a cross-section with a single, consistent diameter. The upper portion of the central pipe 202 is configured with a series of parallel venting grooves 204 that are cut or molded or otherwise formed into the surface of the central pipe 202 to form shallow, partial-depth vent channels into the outer surface of the central pipe 202. A plurality of the grooves 204 may be arranged around a circumference of the central pipe 202. As also illustrated in FIG. 4, the central pipe 202 is configured with a series of proximal vent holes 203 for the passage of gas bubbles from the central pipe 202b (at the proximal holes 203). The escaping gas bubbles are captured and retained by the float 210, and are later vented (during each float cycle) at the venting grooves 204 when the float 210 is elevated. Optionally, the central pipe 202 may include one or more distal vent holes 205 that limit the maximum air pressure that can be achieved inside the central pipe 202 (and, therefore, in the exhalation limb 108) regardless of the pressure setting at the regulator 216.

As illustrated in FIGS. 4 and 5, the float 210 comprises an inner sleeve 402 that includes two series of openings 404, 406 for the passage of air bubbles, into and out of, the float 210, respectively. Optionally, and as noted above, the series of upper openings 406 and lower openings 404 are combined into a series of slot-like openings. A lower series of openings 404 are arranged in the inner sleeve 402 to correspond to the holes 203 in the central pipe 202. This correspondence need not be exact, so long as air venting from holes 203 in the central pipe 202 pass through the lower openings 404 and into an interior space 410 of the float 210. The interior space 410 is configured for temporarily retaining the gas bubbles. When the float 210 is negatively buoyant and resting in a first or lowered position, the sleeve 402 will be positioned with respect to the central pipe 202 such that gas bubbles escaping from the proximal holes 203 will enter the lower series of openings 404 to be retained within the inner space of the float 210. An upper series of openings 406 are similarly arranged around the inner sleeve 402 and are configured to correspond to the vent grooves 204 in the central pipe 202. Again, as noted above, this correspondence need not be exact, so long as air venting from the interior space 410 of the float 210 passes through the upper openings 406 to grooves 204 in the central pipe 202.

When the float 210 is positively buoyant and floating in a second or elevated position, the sleeve 402 will be positioned with respect to the central pipe 202 such that gas retained in the interior space 410 of the float 210 (from the escaping gas bubbles) will be allowed to escape through the upper series of openings 406 via the grooves 204. That is, a properly positioned upper series of openings 406 of the sleeve 402 with respect to the vent grooves 204 of the central pipe 202, form a series of vent channels through which the gas bubbles escape out of the interior space 410 of the float 210 when the float 210 is elevated. Such entry and exit of the gas bubbles into and out of the interior space 410 of the float 210 allows for the variable buoyancy of the float 210. It will be appreciated that the above-described principle of a single pipe designed to provide venting channels for a variable buoyant float can be readily implemented in other forms, without departing from the spirit and scope of the present invention.

As illustrated in FIG. 5, when the float 210 is slid over the central pipe 202, the diameter of the inner sleeve 402 is such that the inner sleeve 402 fits sufficiently snugly against the central pipe 202 to substantially prevent air from escaping between the sleeve 402 and the pipe 202 when the float is below its elevated position, but the inner sleeve 402 is also sufficiently loose to permit substantially free sliding of the float along its pipe, preferably without undue friction. As also illustrated in FIG. 5, the diameter of the inner sleeve 402 is such that when the float 210 is floating, buoyant, in the upper, second position, the holes 203 in the corresponding central pipe 202 will be occluded (blocked, such that gas bubbles are not allowed to escape via the proximal holes 203).

Note that inner sleeve 402 can be fashioned of various materials, such as metal or plastic. Also, the sleeve 402 can be formed from multiple components. For example, in the present embodiment, the inner diameter of the washer 218 forms the upper edge of the inner sleeve 402.

Figure 7:
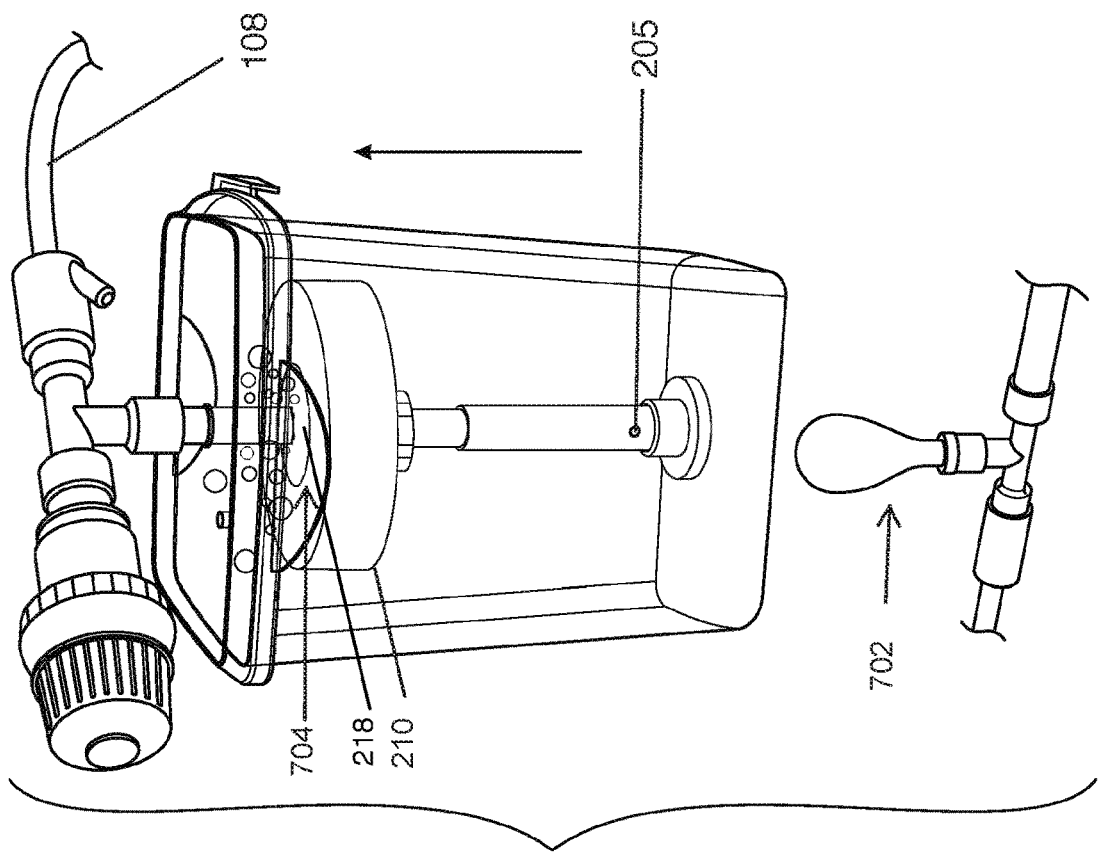
FIG. 7 is another side perspective view of the dual-pressure respiratory assistance device of FIG. 2, illustrating the float in a second position providing a high, peak pressure level when the sleeve of the float occludes the proximal vent holes in the central pipe, not allowing air bubbles to escape.
Figure 6:
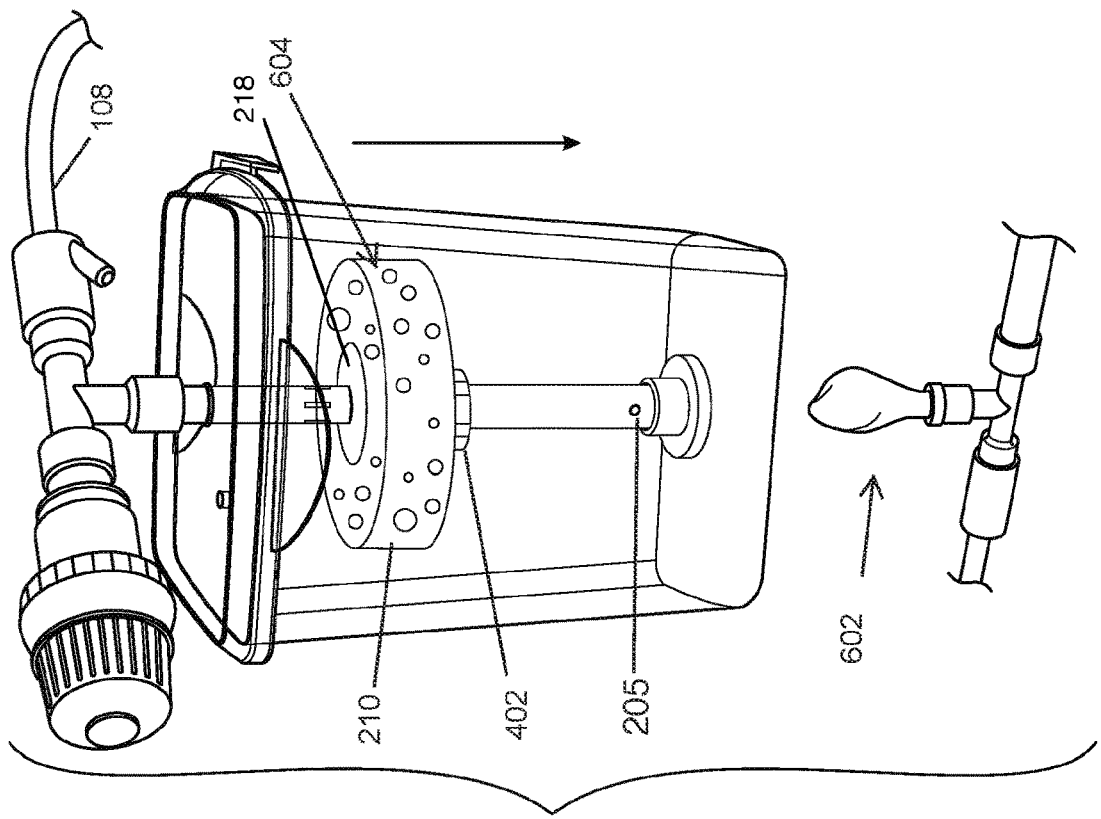
FIG. 6 is a side perspective view of the dual-pressure respiratory assistance device of FIG. 2, illustrating a float in a first position providing a low, baseline pressure level when a sleeve of the float exposes proximal vent holes in the central pipe, allowing air bubbles to escape.

Referring to FIGS. 6 and 7, and as discussed herein, the float 210 is configured to cycle through the water between the first lower position (in which the weight due to gravity is greater than the buoyancy of the float, alternatively abbreviated as the "negative buoyancy" position, and the second, higher position (in which the weight due gravity is less than the buoyancy of the float, alternately abbreviated as the "positive buoyancy" position). As illustrated in FIG. 6, when the float 210 is negatively buoyant, the float 210 has sunk through the water to the first position. Because of the weighted washer 218 (or denser-than-water material selected for the float 210 and/or inner sleeve 402), when the float 210 is sufficiently empty of retained gas, the float 210 will have a negative buoyancy. As illustrated in FIG. 7, when the float 210 is positively buoyant due to the accumulation of bubbles in the umbrella-like interior space 410, the float 210 has risen through the water to the second position.

As illustrated in FIGS. 4, 5, and 6, when the float 210 is in the lower first position (the negative buoyancy position), the proximal holes 203 of the central pipe 202 are oriented with respective lower openings 404 in the inner sleeve 402 of the float 210. When the proximal holes 203 in the central pipe 202 are oriented with the lower openings 404 of the inner sleeve 402 of the float 210, gas in the central pipe 202 is allowed to escape as gas bubbles (that is, the sleeve 402 of the float 210 will not occlude the proximal holes 203). The escaping gas bubbles 604 are captured and retained by the float 210 (see FIG. 6). The escaping gas (at the proximal holes 203) maintains the respiratory delivery system pressure at the lower, baseline pressure level (such as a prescribed low pressure level) while the float 210 is at the lower first position and bubbles are escaping from the proximal vent holes 203, (setting the air-water meniscus level in the central pipe 202 at the vent holes 203). The lower, baseline pressure level is illustrated with a partially-deflated balloon or test lung 602 (FIG. 6, inset), which can be used as a simple visual pressure indicator during setup of the system. It will be appreciated that the time duration of the baseline pressure level may be selected by the size of the float's air chamber and the float's natural buoyancy, which affect the time duration required to cause a non-buoyant float to fill with sufficient air to cause it to achieve sufficient positive buoyancy to rise above the first (lower) position along the central pipe 202.

As illustrated in FIGS. 4, 5, and 7, when the float 210 is in the upper second position (the positive buoyancy position), the grooves 204 of the central pipe 202 are aligned with upper openings 406 of the inner sleeve 402 of the float 210. When the grooves 204 of the central pipe 202 are aligned with the upper openings 406 of the inner sleeve 402 of the float 210, gas bubbles 704 retained in the float 210 are allowed to escape via channels created by the orientation or position of the upper openings 406 of the inner sleeve 402 with the grooves 204 of the central pipe 202. When the float 210 is in the second position, the inner sleeve 402 of the float 210 is positioned to occlude the proximal holes 203 in the central pipe 202. With the proximal holes 203 occluded, gas is retained within the central pipe 202 (unable to escape through the proximal vent holes 203) and the pressure delivered by the respiratory assistance device rises to the higher, peak pressure level (such as a prescribed high pressure level) as determined by the pressure regulator 216, with the water meniscus located well below the proximal vent holes 203 (but not reaching as far down as the distal vent holes 205 unless high pressure level is set too high at the regulator 216). The higher, peak pressure level is illustrated with a more inflated balloon or test lung 702 (FIG. 7, inset), which can be used as a simple visual pressure indicator during setup of the system. It will be appreciated that the time duration of the peak pressure level may be selected by the size of the upper openings 406 and/or the vent grooves 204, which control the rate at which trapped air is released from the float 210 and, therefore, the "dwell time" at which the float remains in the second (elevated) position. It will further be appreciated that the float 210 may incorporate or define its own gas-venting opening that "leaks" collected gas at a desired rate, which can also provide a slower cycling rate by slowing the rate at which the float collects gas while in its lower position. The gas-venting opening in the float may be a fixed-size opening with an optional plug so that its use is discretionary, or may be an adjustable opening or valve that allows a user to change the rate at which gas is vented from the float even while it is in the lower position.

As illustrated in FIGS. 6 and 7, when the float 210 is resting in the first position (such that the lower openings 404 of the inner sleeve 402 of the float 210 are oriented with the proximal holes 203 of the central pipe 202), gas bubbles are exiting from the central pipe 202 (via the proximal holes 203) and are retained by the float 210 and changing the buoyancy of the float 210 until the float 210 is buoyant enough to float up to the second position. When the float's buoyancy has increased sufficiently to float up to the second position (positively buoyant), the proximal holes 203 in the central pipe 202 will be occluded by the inner sleeve 402 of the float 210. As also illustrated in FIGS. 6 and 7, when the float 210 is floating in the second position (such that the upper openings 406 of the inner sleeve 402 of the float 210 are oriented with the grooves 204 of the central pipe 202), gas bubbles are escaping from the float 210 (via the grooves 204) and reducing the buoyancy of the float 210 until the float 210 is negatively buoyant and sinks down to the first position.

Of note, there is a possible intermediate position between the lower first position and the higher second position of float 210 sliding on the central pipe 202. After the float 210 rises from the lower first position, the inner sleeve 402 may occlude the proximal venting holes 203 on the central pipe 202 before the float 210 has risen sufficiently for the upper openings 406 of the inner sleeve 402 to align with the grooves 204 on the central pipe 202 and release the air. This may be considered the "intermediate position." Soon thereafter, the float 210 will rise such that the inner openings 406 of the inner sleeve 402 align with the grooves of the central pipe 202, forming an air channel through which the gas collected in the float 210 is released.

Thus, the float 210 is configured to float between a first position which results in a lower, baseline pressure level, and a second position, which results in a higher, peak pressure level. The float 210 retaining gas bubbles via the aligned holes 203 and lower openings 404, and losing gas bubbles via the aligned grooves 204 and the upper openings 406, results in the float 210 cycling between the negatively buoyant first position and the positively buoyant second position. The rate of oscillation or cycling may be adjusted by varying the air flow rate at the air supply 102. The higher the air flow rate at the air supply 102, the faster the bubbles will escape through the proximal vent holes 203 and the faster the resulting cycling rate. Cycling rate can also be increased by providing large grooves or vent channels to quickly release entrapped air when the float reaches the second position. Optionally, a calibrated gas vent in the float 210 can increase the time required to fill the float 210 with air from the proximal vent holes 203 in the central pipe 202, increasing the time the float 210 stays in the lower first position and lower the cycling rate. In one embodiment of the present invention, a setting of 4 L/min flow rate (at the air supply 102) will realize approximately 20 cycles per minute. Similarly, a setting of 8 L/min (at the air supply 102) will realize approximately 40 cycles per minute.

As illustrated in FIGS. 8A, 8B, and 8C, the high or peak pressure level may be adjusted via the pressure regulator 216. When the float 210 is in the buoyant second position, the inner sleeve 402 of the float 210 is positioned to occlude the proximal holes 203 in the central pipe 202. With the proximal holes 203 occluded, gas is retained within the central pipe 202 (unable to escape from the vent holes 203) and the pressure delivered in the respiratory conduit rises to the higher, peak pressure level, which results in the water meniscus level in the central pipe 202 dropping below the vent holes 203 by a distance corresponding to the pressure regulator setting. This higher, peak pressure level is adjustable (at the pressure regulator 216) within the limits of the length of the central pipe 202. As illustrated in FIGS. 3, 8A, 8B, and 8C, distal vent holes 205 in the central pipe 202 are configured to limit the maximum peak gas pressure that can be achieved, regardless of the pressure regulator setting (this is contingent on the distal vent holes 205 having a sufficient cross sectional area to prevent a throttling effect, in which all the pressure of the system is not fully released through these holes). That is, if the regulator pop-off pressure is set so high that the air-water meniscus layer 802 lowers down to the distal vent holes 205, the gas in the central pipe 202 will escape out the distal vent holes 205, and the peak pressure is unlikely to exceed the maximum defined by the distance between the distal vent holes 205 and the upper surface of the water column. For the example, the distal holes 205 may be set to a depth of 25 cm, which would limit the maximum possible peak pressure level to 25 cm $H_2O$, even if the regulator 216 is capable of achieving higher pressures of 26 cm $H_2O$ or more.

The pressure regulator 216 is configured to vary the peak pressure in the respiratory delivery system 100. In one exemplary embodiment, the pressure regulator 216 is an adjustable pop-off valve that releases the pressure above an adjustable set point, to prevent the peak pressure level from exceeding the set point (e.g., a setting of 8-25 cm). As illustrated in FIGS. 8A, 8B, and 8C, when the peak pressure level is adjusted, an air-water meniscus 802a, 802b, and 802c level will be adjusted accordingly. This meniscus provides a mechanism for dynamic visualization of delivered pressure in the respiratory system: users can visualize the transition from low pressure to high pressure, the high pressure level and the transition from high pressure to low pressure. The higher the peak pressure level, the lower the air-water meniscus level 802 will be in the central pipe 202 (see FIGS. 8A and 8B). As illustrated in FIG. 8C, when the peak pressure level is such that the air-water meniscus level 802c is below the distal holes 205 (that is, below an exemplary 25 cm), air bubbles will escape from the distal vent holes 205 and the peak pressure will be prevented from going any higher. The distal vent holes 205 can be incorporated in a modified anchor 214 instead of in the central pipe 202 for similar function.

Optionally, the distal vent holes 205 may be omitted from the central pipe 202. This design can be produced much more compactly as the higher level of pressure is no longer determined hydrostatically by the height of the water column. A manometer can be fluidly connected with the respiratory conduit for visually measuring the varying pressure level settings. The system may also be fitted with a separate safety system designed to release pressure if it exceeds a set threshold. In one exemplary embodiment, the peak pressure level may be adjusted to 8-25 cm $H_2O$.

As noted herein, embodiments of the present invention provide for improved adjustments and control of a dual pressure respiratory assistance device, such that a baseline pressure level and peak pressure level may be easily set. Such embodiments allow for a low cost, low tech solution that uses available distilled water, and an available compressed air source (such as providing 4-8 L/min of air). Once the respiratory device 200 has been assembled as discussed herein, filled with water for a desired column of water height, and coupled to the air source, the respiratory device 200 is placed near the patient, and the patient interface 106 is connected to the patient. It may be desirable to place the respiratory device 200 at an elevation that is below the elevation of the patient so that any liquid that is inadvertently present in the exhalation limb 108 does not reach the patient's lungs. At this point, the air flow rate at the air supply 102 may be set to a flow rate for a desired cycle rate (e.g., 20-40 cycles per minute), while the peak pressure level is set by selecting a pressure set point on the pressure regulator 216, which may be visually confirmed with the use of a pressure manometer in the central pipe 202. The lower baseline level of pressure is set by the amount of water in the container 207, which determines the depth of the hydrostatic water column. Thereafter, the peak pressure level of the respiratory device 200 may be adjusted via the pressure regulator 216 as needed.

Changes and modifications in the specifically described embodiments can be carried out without departing from the principles of the present invention which is intended to be limited only by the scope of the appended claims, as interpreted according to the principles of patent law including the doctrine of equivalents.

The invention claimed is:

1. A respiratory delivery system providing a bi-level pressure, the respiratory delivery system comprising:
    a container configured to support a volume of liquid;
    a pipe disposed in said container and configured to be at least partially submerged into the volume of liquid, said pipe defining at least one vent opening at a midsection thereof, wherein said pipe is configured to receive a flow of breathable gas from a gas source;
    a variable buoyancy float disposed along said pipe and inside said container, said float configured to cyclically float up and down said pipe between a lower position and a higher position, wherein said at least one vent opening is occluded by said float in the higher position; and
    an adjustable pressure regulator in fluid communication with said pipe;
    wherein said float is configured to cyclically shift a pressure level of the breathable gas in said respiratory delivery system between a baseline pressure level when said float is in the lower position and gas bubbles are permitted to escape from said at least one vent opening, and a peak pressure level that is higher than the baseline pressure level when said float is in the higher position and said at least one vent opening is occluded by said float; and wherein the peak pressure level is defined by a setting of said adjustable pressure regulator.

2. The respiratory delivery system of claim 1, wherein the peak pressure level defined by said adjustable pressure regulator corresponds to an air/water meniscus layer in said pipe that is below the depth of said at least one vent opening in said pipe.

3. The respiratory delivery system of claim 2, wherein said float comprises an inner sleeve configured to slide along said pipe, wherein said inner sleeve occludes said at least one vent opening in said pipe when said float is floating in the higher position, and wherein said inner sleeve of said float comprises at least one lower opening configured to align with said at least one vent opening and allow gas bubbles to escape from said at least one vent opening when said float is resting in the lower position.

4. The respiratory delivery system of claim 3, wherein said inner sleeve of said float comprises an upper opening configured to allow gas bubbles retaining in said float to escape from said float in the higher position.

5. The respiratory delivery system of claim 4, wherein said pipe comprises at least one groove positioned above said at least one vent opening, and wherein said upper opening of said inner sleeve of said float is aligned with said at least one groove when said float is in the higher position, and wherein said at least one groove and said upper opening cooperate to form a vent channel through which the gas bubbles escape from said float in the higher position.

6. The respiratory delivery system of claim 1, wherein said float comprises a weight, wherein said float is configured to capture and retain the gas bubbles escaping from said at least one vent opening in said pipe, wherein the retained gas bubbles raise the buoyancy of said float, and wherein said float has a negative buoyancy when retaining substantially no gas bubbles.

7. The respiratory delivery system of claim 1, wherein said pressure regulator is an adjustable pop-off valve configured to prevent the pressure level of said respiratory delivery system from rising above a selected pressure level set point of said pop-off valve.

8. The respiratory delivery system of claim 1, wherein said pipe comprises a distal vent hole at a depth below said at least one vent opening, and wherein said distal vent hole is configured to allow gas bubbles to escape from said pipe when an air/water meniscus layer drops to the depth of said distal vent hole, and wherein a maximum pressure level of said respiratory delivery system is limited by the depth of said distal vent hole below an upper surface of the volume of liquid in said container.

9. The respiratory delivery system of claim 1, wherein the pressure level of said respiratory delivery system is at the baseline pressure level for a first period of time and at the peak pressure level for a second period of time that is less than the first period of time, and wherein said respiratory delivery system transitions from the baseline pressure level to the peak pressure level in a period of transition time that is less than each of the first and second periods of time.

10. The respiratory delivery system of claim 1, wherein the baseline pressure level is a baseline pressure range, and wherein the peak pressure level is a peak pressure range, and wherein the baseline pressure range is 5-8 cm $H_2O$, and wherein the peak pressure range is 8-25 cm $H_2O$.

11. The respiratory delivery system of claim 1, wherein said float comprises an open-bottom enclosure disposed above and around said at least one vent opening, such that gas released from said at least one vent opening travels upwardly through the liquid and into said enclosure.

12. The respiratory delivery system of claim 1, wherein said pipe comprises a pressure manometer configured to provide a visual indication of the baseline pressure level, the peak pressure level, and a transition pressure between the baseline and peak pressure levels.

13. The respiratory delivery system of claim 1, wherein said pipe and said adjustable pressure regulator are configured to be coupled to an exhalation limb positioned downstream of a patient interface and the gas source.

14. The delivery system of claim 1, wherein said pipe is mounted in an upright orientation and an anchor is coupled to a lower end portion of said pipe, wherein said anchor defines an opening configured to permit the liquid into and out of said lower end portion of said pipe.

15. The delivery system of claim 1, wherein said float comprises a gas-venting opening that permits a limited flow of the breathable gas out of said float in the lower position.

16. A respiratory delivery system providing a bi-level pressure, the respiratory delivery system comprising:
a container configured to support a volume of liquid;
a lid configured to be secured to an upper end of said container, said lid defining an opening;
a pipe mounted in said container and configured to be at least partially submerged into the volume of liquid, said pipe having a lower end secured to a bottom surface of said container and an upper end portion supported in said opening, said pipe defining at least one vent opening at a midsection thereof, and said pipe defining a sidewall recess above said at least one vent opening, wherein said pipe is configured to receive a flow of breathable gas from a gas source;
a variable buoyancy float disposed along said pipe inside said container, said float configured to cyclically float up and down said pipe between a lower position and a higher position above said lower position, wherein when said float is in said higher position said at least one vent opening is occluded by said float and said sidewall recess is at least partially overlapped by said float; and
an adjustable pressure regulator in fluid communication with said pipe and with the gas source;
wherein said float is configured to cyclically shift a pressure level of said respiratory delivery system between a baseline pressure level when said float is in said lower position and gas bubbles are permitted to escape from said at least one vent opening, and a peak pressure level that is higher than said baseline pressure level when said float is in said higher position; and
wherein said peak pressure level is defined by a setting of said adjustable pressure regulator.

17. The respiratory delivery system of claim 16, wherein said adjustable pressure regulator comprises a pop-off valve configured to prevent the pressure level of said respiratory delivery system from rising above a selected pressure level set point of said pop-off valve.

18. The respiratory delivery system of claim 16, wherein said float comprises an open-bottom enclosure disposed above and around said at least one vent opening, such that gas released from said at least one vent opening travels upwardly through the liquid and into said enclosure.

19. The respiratory delivery system of claim 16, wherein said tube comprises a pressure manometer configured to provide a visual indication of the baseline pressure level and the peak pressure level.

20. The respiratory delivery system of claim 16, wherein said float comprises an inner sleeve configured to slide along said pipe, said inner sleeve defining a lower opening configured to align with said at least one vent opening and allow gas bubbles to escape from said at least one vent opening when said float is resting in the lower position, and said inner sleeve further defining an upper opening configured to align with said sidewall recess in said pipe to form a vent channel through which the gas bubbles escape from said float in the higher position.

* * * * *